United States Patent
Abraham et al.

(10) Patent No.: US 11,730,627 B2
(45) Date of Patent: Aug. 22, 2023

(54) SYSTEMS AND METHODS FOR ALIGNING AN EYE WITH A PATIENT INTERFACE OF AN OPHTHALMIC LASER DEVICE

(71) Applicant: Alcon Inc., Fribourg (CH)

(72) Inventors: Mario Abraham, Burgthann (DE); Michael Wittnebel, Hirschaid (DE)

(73) Assignee: Alcon Inc., Fribourg (CH)

( * ) Notice: Subject to any disclaimer, the term of this patent is extended or adjusted under 35 U.S.C. 154(b) by 169 days.

(21) Appl. No.: 17/408,548

(22) Filed: Aug. 23, 2021

(65) Prior Publication Data

US 2022/0062039 A1    Mar. 3, 2022

Related U.S. Application Data (60) Provisional application No. 63/071,768, filed on Aug. 28, 2020.

(51) Int. Cl.
*A61F 9/009* (2006.01)
*A61F 9/008* (2006.01)

(52) U.S. Cl.
CPC .......... *A61F 9/009* (2013.01); *A61F 9/00827* (2013.01); *A61F 2009/00872* (2013.01); *A61F 2009/00882* (2013.01)

(58) Field of Classification Search
CPC ...... A61F 9/009; A61F 9/00827; A61F 9/008; A61B 3/0025; A61B 3/0083; A61B 3/152
USPC .......................................................... 606/4
See application file for complete search history.

(56) References Cited

U.S. PATENT DOCUMENTS

| | | |
|---|---|---|
| 2013/0050649 A1 | 2/2013 | Juhasz et al. |
| 2014/0069439 A1 | 3/2014 | De Juan, Jr. et al. |
| 2015/0005754 A1* | 1/2015 | Gooding ................. A61B 18/20 606/6 |
| 2016/0095752 A1* | 4/2016 | Srinivasan .......... A61F 9/00834 606/6 |
| 2016/0106582 A1* | 4/2016 | Campos .................. A61F 9/009 606/4 |
| 2018/0036168 A1* | 2/2018 | Heitel ..................... A61F 9/008 |
| 2020/0253781 A1* | 8/2020 | Pössel ..................... A61F 9/009 |

FOREIGN PATENT DOCUMENTS

| | | |
|---|---|---|
| EP | 2606864 A1 | 6/2013 |
| EP | 2611400 A1 | 7/2013 |

OTHER PUBLICATIONS

Wikipedia, "Femtosekunden-Lentikel-Extraktion", Editing Status: Jan. 21, 2020. Retrieved Aug. 18, 2021.
Wikipedia, "Rotationsellipsoid", Editing Status: Jan. 17, 2020. Retrieved Aug. 23, 2021.

* cited by examiner

*Primary Examiner* — Eric D. Bertram
*Assistant Examiner* — Michael T. Holtzclaw (57) ABSTRACT

In certain embodiments, a system for aligning an eye with a patient interface of a laser device includes a camera, a display screen, and a computer. The camera records images of the eye through the patient interface of the laser device. A liquid is disposed between and is in contact with the patient interface and the outer surface of the eye. The images include an outline of the liquid. The display screen displays the images of the eye. The computer aligns the eye with the patient interface by: identifying the outline of the liquid in an image received from the camera; determining a misalignment of the eye according to the outline; and instructing the display screen to display a description of the misalignment.

20 Claims, 8 Drawing Sheets

SYSTEMS AND METHODS FOR ALIGNING AN EYE WITH A PATIENT INTERFACE OF AN OPHTHALMIC LASER DEVICE

TECHNICAL FIELD

The present disclosure relates generally to ophthalmic laser devices, and more particularly to aligning an eye with a patient interface of an ophthalmic laser device.

BACKGROUND

Certain ophthalmic laser surgical systems have a laser device that generates a pulsed laser beam to perform a surgical procedure on an eye. In some procedures, the laser beam creates photodisruptions at specific points in the eye according to a treatment pattern. The laser beam should be properly aligned with the eye to create photodisruptions that precisely match the pattern. A patient interface (PI) coupled to the laser device is usually used to align the laser beam with the eye during the procedure. The patient interface is typically affixed to the eye by a vacuum to secure the eye in place to properly position the eye relative to the treatment pattern.

Aligning the eye with the patient interface to couple the interface onto the eye in the proper position, i.e., to "dock" the interface onto the eye, is non-trivial. According to one known docking process, the patient is asked to gaze at a fixation light concentric with the laser beam, and then the surgeon manually positions the interface onto the eye. However, patients often have difficulty gazing into the fixation light, especially once the interface makes contact with the eye, reducing the accuracy of the alignment. According to another known docking process, the pupil of the eye can be imaged and used to align the patient interface with the eye. However, some types of patient interfaces may distort the pupil as the interface is placed onto the eye, reducing the accuracy of the alignment. These known processes may result in faulty positioning of the interface on the eye such that, e.g., the laser beam is not centered on the eye and/or is at an angle to the axis of the eye. For certain procedures, the misalignment may yield a sub-optimal result. For example, in a lenticular extraction procedure, a lenticule created with a misaligned laser beam may be not centered at and/or at an angle to the axis of the eye, resulting in sub-optimal vision correction.

BRIEF SUMMARY

In certain embodiments, a system for aligning an eye with a patient interface of a laser device includes a camera, a display screen, and a computer. The camera records images of the eye through the patient interface of the laser device. A liquid is disposed between the patient interface and the outer surface of the eye. The liquid is in contact with the patient interface and with the outer surface of the eye. The images include an outline of the liquid. The display screen displays the images of the eye. The computer aligns the eye with the patient interface in order to align the eye with a laser beam of the laser device. The eye is being aligned to perform a procedure on the eye according to a treatment pattern. The computer aligns the eye with the patient interface by: identifying the outline of the liquid in an image received from the camera; determining a misalignment of the eye according to the outline; and instructing the display screen to display a description of the misalignment.

Embodiments may include none, one, some, or all of the following features:

The computer determines the misalignment of the eye according to the outline by: identifying that a shape of the outline is an oval; and determining that an axis of the eye is at an angle to a z-axis of the laser device.

The computer determines the misalignment of the eye according to the outline by: determining that a centroid of a shape of the outline not at a center point of the laser device; and determining that the eye is laterally displaced with respect to the center point of the laser device.

The computer determines an adjustment that substantially compensates for the misalignment. For example, the computer determines the adjustment that substantially compensates for the misalignment by: identifying that a shape of the outline is an oval; determining that an axis of the eye is at an angle to a z-axis of the laser device in response to identifying the shape; and determine that rotating the eye substantially compensates for the misalignment. For example, the computer determines the adjustment that substantially compensates for the misalignment by: determining that a centroid of a shape of the outline not at a center point of the laser device; determining that the eye is laterally displaced a distance with respect to the center point of the laser device; and determining that translating the eye the determined distance towards the center point substantially compensates for the misalignment. In certain embodiments, the computer instructs the display screen to display a description of the adjustment. In certain embodiments, the computer adjusts the patient interface or the eye according to the adjustment to compensate for the misalignment. In certain embodiments, the computer adjusts the treatment pattern according to the adjustment to compensate for the misalignment.

The computer: generates an alignment overlay that indicates a desired position and a desired shape of the outline that aligns the eye with the patient interface; places the alignment overlay onto the images; and instructs the display screen to display the images with the alignment overlay. In certain embodiments, the computer: receives a description of a corneal topography of the eye; and determines the desired position and the desired shape of the outline that aligns the eye with the patient interface according to the corneal topography of the eye. In certain embodiments, the computer: determines a plurality of alignment overlays, each alignment overlay corresponding to a specific distance between the eye and the patient interface; determines the distance between the eye and the patient interface; and generates the alignment overlay corresponding to the determined distance.

The computer determines a distance between the eye and the patient interface according to a size of the outline. In certain embodiments, the computer instructs the display screen to display the distance between the eye and the patient interface. In certain embodiments, the computer adjusts the distance of the eye from the patient interface in response to the determined distance between the eye and the patient interface.

The computer performs a liquid distribution procedure to redistribute the liquid by: moving the patient interface farther away from the eye; and moving the patient interface closer to the eye.

The system further comprises a dispenser configured to dispense additional liquid onto the outer surface of the eye. The computer instructs the dispenser to dispense the additional liquid onto the outer surface of the eye. In certain embodiments, the additional liquid comprises a substance that can change a surface tension of the liquid. In certain embodiments, the additional liquid comprises a substance that enhances the visibility of the liquid.

The system further comprises a vacuum device configured to remove at least a portion of the liquid from the outer surface of the eye. The computer instructs the vacuum device to remove at least the portion of the liquid from the outer surface of the eye.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain ophthalmic surgical procedures, the eye is coupled to a surgical system with a patient interface (PI) in order to properly align the eye with a treatment pattern. An issue may arise in that aligning the eye with the patient interface in order to affix the interface to the eye can be difficult. Certain embodiments may address this issue.

Figure 1:
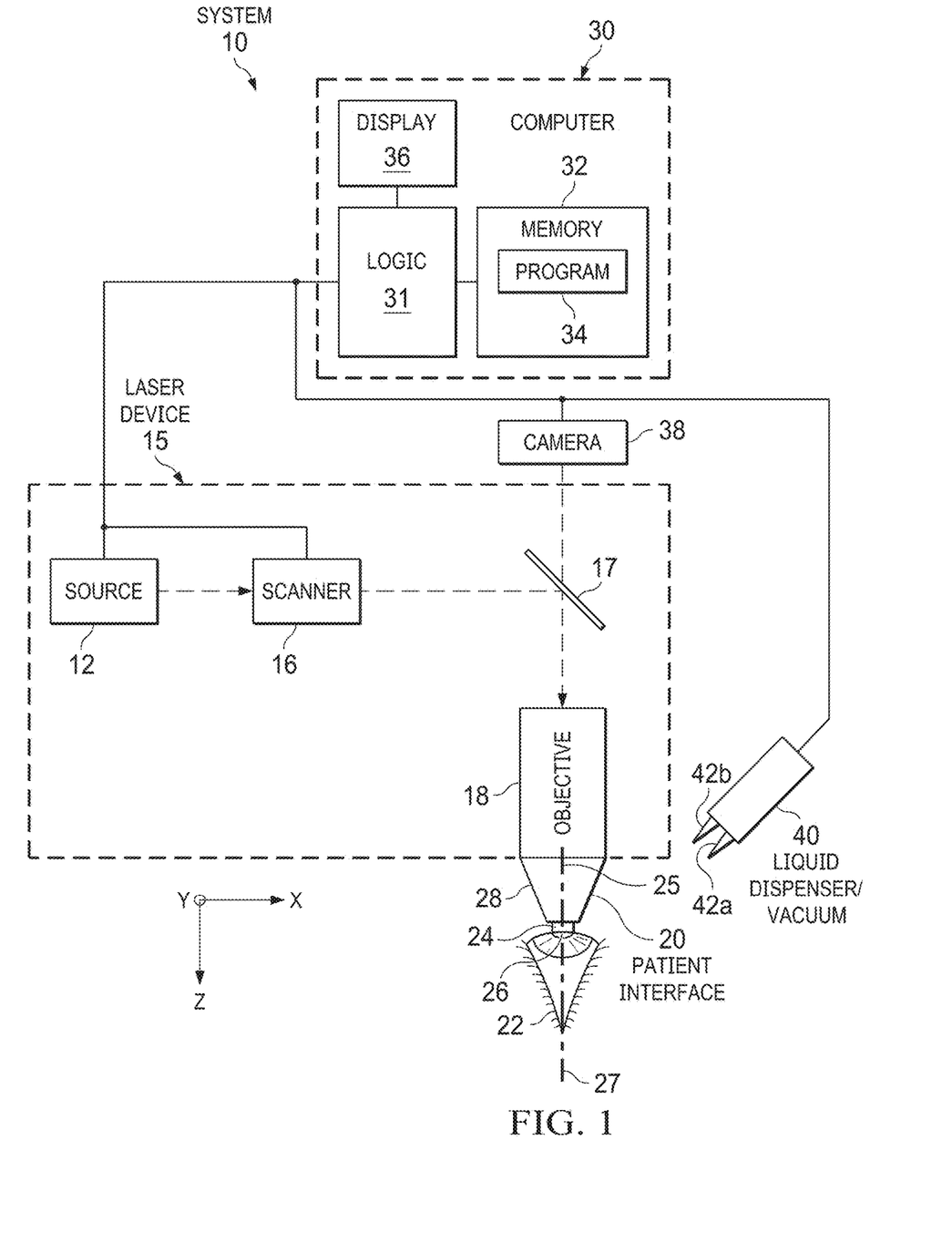
FIG. 1 illustrates an example of an ophthalmic surgical system configured to align an eye with a patient interface according to certain embodiments.

FIG. 1 illustrates an example of an ophthalmic surgical system 10 configured to align an eye 22 with a patient interface 20 according to certain embodiments. In the embodiments, system 10 images a liquid (not shown) disposed between patient interface 20 and eye 22. The outline of the liquid indicates the alignment of eye 22 relative to patient interface 20. System 10 uses the outline of the liquid to align eye 22 with interface 20 during the docking process. Accordingly, system 10 may address the issue of affixing patient interface 20 to eye 22 such that an eye is aligned with the treatment pattern.

In general, aligning eye 22 with patient interface 20 refers to positioning eye 22 relative to patient interface 20 (or patient interface 20 relative to eye 22) such that, when interface 20 is affixed to eye 22, a laser beam passing through interface 20 strikes eye 22 at the appropriate point and angle of eye 22 according to the treatment pattern. Note that "aligning eye 22 with patient interface 20" also includes aligning patient interface 20 with eye 22. In certain embodiments, alignment may be described according to the xyz-coordinate system of a laser device of system 10, where a centered laser beam defines the z-axis and an abutment face of patient interface 20 defines the xy-plane at z=0. In the embodiments, the center point (x, y, z)=(0, 0, 0) and central axis z=0 (or z-axis) of patient interface 20 (and thus of laser device 15) is aligned with a center point (e.g., pupil center, eye apex, or eye vertex) and a central axis (e.g., optical axis or visual axis), respectively, of eye 22. However, any suitable features of patient interface 20 may be aligned with any suitable features of eye such that the laser beam strikes at the appropriate parts of eye 22 according to the treatment pattern.

Misalignment may occur in a number of different ways: (1) eye 22 may be laterally misaligned by a lateral displacement the x and/or y directions; (2) eye 22 may have a rolling misalignment such that the axes of eye 22 and interface 20 are not aligned, i.e., the axes are at an angle greater than zero degrees (e.g., greater than three degrees) relative to each other; (3) eye 22 may be torsionally misaligned by a rotational displacement about the z-axis; and (4) eye 22 may be longitudinally misaligned by a longitudinal displacement the z direction.

In the illustrated example, system 10 includes a laser device 15, a patient interface 20 (with and axis 25), a camera 38, a liquid dispenser/vacuum 40, and a control computer 30, coupled as shown. Laser device 15 includes controllable components, such as a laser source 12, a scanner 16, one or more optical elements 17, and/or a focusing objective 18, coupled as shown. Patient interface 20 includes a contact portion 24 (with an abutment face 26) and a sleeve 28 coupled as shown. Computer 30 includes logic 31, a memory 32 (which stores a computer program 34), and a display 36, coupled as shown. Eye 22 has an axis 27.

As an overview, system 10 aligns eye 22 with patient interface 20 according to the following example of operation to allow the laser beam of laser device 15 to perform a procedure on eye 22 according to a treatment pattern. Camera 38 records images of eye 22 through patient interface 20. A liquid (e.g., tear film) is disposed between patient interface 20 and the outer surface of eye 22, where the liquid is in contact with patient interface 20 and the outer surface. The images include an outline of the liquid. Display 36 displays the images of the eye. Computer 30 identifies the outline of the liquid in an image received from camera 38; determines a misalignment of eye 22 according to the outline; and instructs display 36 to display a description of the misalignment.

Turning to the parts of system 10, laser source 12 generates a laser beam with ultrashort pulses. An ultrashort pulse refers to a light pulse that has a duration that is less than a nanosecond, such as on the order of picoseconds, femtoseconds, or attoseconds. The laser beam may have any suitable wavelength, such as a wavelength in the range of 300 to 1500 nanometers (nm), for example, a wavelength in the range of 300 to 650, 650 to 1050, 1050 to 1250, and/or 1250 to 1500 nm, such as 340 to 350 nm, e.g., 347 nm±1 nm. The focal point of the laser beam may create a laser-induced optical breakdown (LIOB) in tissue (e.g., the cornea) to yield a photodisruption in the tissue. The laser beam may be precisely focused to yield precise photodisruptions, which may reduce or avoid unnecessary destruction of other tissue.

Scanner 16 laterally and longitudinally directs the focal point of the laser beam. The longitudinal direction refers to the direction of the laser beam propagation, also known as the z-direction. The lateral direction refers to directions orthogonal to the direction of beam propagation, also known as the xy-plane. In certain embodiments, the xyz-coordinate system of laser device 15 is defined as: abutment face 26 of patient interface 20 is the xy-plane at z=0, and the center of abutment face 26 is the z-axis at (x, y)=(0, 0). Other suitable xyz-coordinate systems may be used.

Scanner 16 may laterally direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam. Scanner 16 may longitudinally direct the laser beam in any suitable manner. For example, scanner 16 may include a longitudinally adjustable lens, a lens of variable refractive power, or a deformable mirror that can control the z-position of the beam focus. The components of scanner 16 may be arranged in any suitable manner along the beam path, e.g., in the same or different modular units.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Patient interface 20 interfaces with the cornea of eye 22 to couple eye 22 to laser device 15. In the example, patient interface 20 has sleeve 28 coupled to contact portion 24. Sleeve 28 detachably couples to focusing objective 18. Contact portion 24 may be translucent or transparent to the laser beam and has an abutment face 26 that interfaces with the cornea. In certain embodiments, abutment face 26 is planar and forms a planar area on the cornea, which may define the xy-plane. In other embodiments, abutment face 26 need not be planar, e.g., may be convex or concave. In certain embodiments, patient interface 20 has rotational symmetry with an axis 25, which may be aligned with an axis 27 of eye 22.

Camera 38 records images of the eye 22 through patient interface 20. Examples of camera 38 include a video, eye-tracking, or optical coherence topography (OCT) camera. Camera 38 delivers image data, which represent recorded images of the eye 22, to computer 30. Computer 30 carries out image processing on the image data to identify an outline of a liquid disposed between patient interface 20 and eye 22. The image processing includes recognizing the liquid in the recorded images, determining the outline of the liquid, and identifying the shape of the outline.

Liquid dispenser/vacuum 40 comprises a dispenser and/or vacuum device. A dispenser dispenses additional liquid onto the outer surface of eye 22. The additional liquid may be any suitable substance, such as artificial tears. In certain cases, the additional liquid may include a substance that changes the surface tension of the liquid between eye 22 and interface 20. For example, the surface tension may be decreased such that the liquid film spreads more easily on interface 20. As another example, the surface tension may be increased to make the outline of the liquid smaller. In certain cases, the additional liquid may include a medication for eye 22, e.g., a substance that decreases discomfort or pain. In certain cases, the additional liquid may include a substance that enhances the visibility of the outline. For example, the additional liquid may include a dye that changes the color of the liquid to a more visible color or a dye that includes a fluorescent tracer.

A vacuum device removes at least a portion of the liquid from the outer surface of eye 22, typically using suction. Liquid dispenser/vacuum 40 may have nozzles 42 (42a, 42b) to dispense and/or remove liquid. In the illustrated example, nozzle 42a dispenses liquid and nozzle 42b removes liquid.

Computer 30 controls components of system 10 in accordance with computer program 34. For example, computer 30 controls components (e.g., laser source 12, scanner 16, optical elements 17, and/or focusing objective 18) to focus the laser beam of laser device 15 at eye 22 and to photo-disrupt at least a portion of eye 22 according to a treatment pattern. To successfully treat eye 22, eye 22 must be appropriately aligned with the laser beam. To be appropriately aligned with the laser beam, eye 22 must appropriately affixed to patient interface 20, which requires proper alignment of eye 22 and interface 20 during docking.

In certain embodiments, computer 30 receives images of eye recorded by camera 38 through patient interface 20. A liquid (e.g., tear film) is disposed between patient interface 20 and the outer surface of eye 22, where the liquid is in contact with interface 20 and the outer surface. The liquid forms an outline that is imaged by camera 38. (See FIGS. 2A though 3 for examples of a liquid between eye 20 and interface 20.)

In certain embodiments, computer 30 facilitates aligning eye 22 to patient interface 20 by identifying the shape of the outline of the liquid in an image received from camera 38 and determining a misalignment of eye 22 according to the outline. Computer 30 then instructs display 36 to display a description of the misalignment. For example, computer 30 may identify that the outline is an oval and determine that eye axis 27 is at an angle to interface axis 25 (or the z-axis of laser device 15). As another example, computer 30 may determine that the centroid of the outline not at a center point of laser device 15, and thus determine that eye 22 is laterally displaced with respect to the center point of laser device 15. Examples of the relationship between the outline of a liquid and alignment of eye 22 are described with reference to FIGS. 4A to 7B.

In certain embodiments, computer 30 determines an adjustment that substantially compensates for the misalignment. For example, if eye axis 27 is at an angle to interface axis 25 (or the z-axis of laser device 15), computer 30 may determine that rotating eye 22 substantially compensates for the misalignment. As another example, if eye 22 is laterally displaced a distance with respect to the center point of laser device 15, computer 30 may determine that the following substantially compensates for the misalignment: translating the patient interface; translating the eye; and/or translating the treatment pattern.

In certain embodiments, computer 30 may perform any suitable operation after determining the adjustment. For example, computer 30 may instruct the display 36 to display a description of the adjustment. Examples of descriptions of adjustments are described with reference to FIGS. 9A to 10B. As another example, computer 30 may instruct laser device 15 to adjust patient interface 20 according to the adjustment to compensate for the misalignment. As another example, computer 30 may instruct an automated patient bed to change the position of the patient, such that eye 22 is moved according to the adjustment to compensate for the misalignment. As another example, computer 30 may adjust the treatment pattern according to the adjustment to compensate for the misalignment.

In certain embodiments, computer 30 facilitates aligning eye 22 with patient interface 20 by generating an alignment overlay that indicates the desired position and shape of the outline of the liquid that aligns eye 22 with patient interface 20 and places the alignment overlay onto recorded images of eye 22. Computer 30 then instructs display 36 to display the images with the alignment overlay.

In the embodiments, an alignment overlay indicates a desired position and/or a desired shape (which may also be referred to as an "aligned position and/or aligned shape" or a "predicted position and/or predicted shape") of the outline when eye 22 is aligned with interface 22. An alignment overlay may have any suitable shape or size that indicates desired position and/or desired shape of the outline. For example, the alignment overlay may be one or more shapes that operate as a marker for the center of the outline of the liquid. To align eye 22, eye 22 may be moved relative to interface 20 (or interface 20 is moved relative to eye 22) until the center of the outline of the liquid is at the marker. As another example, the alignment overlay may be a plurality of markers, a circle, or other shape that borders the desired outline of the liquid. To align eye 22, eye 22 may be moved relative to interface 20 (or interface 20 is moved relative to eye 22) until the outline of the liquid is bordered by the overlay. An example of an alignment overlay is described with reference to FIG. 8. In certain embodiments, computer 30 determines an alignment overlay from the corneal topography of eye 22. An example of generating such alignment overlay is described with reference to FIG. 13.

In certain embodiments, computer 30 determines a plurality of alignment overlays, where each alignment overlay corresponds to a distance between eye 22 and patient interface 20. When the docking process reaches a distance, the alignment overlay corresponding to the determined distance is placed onto the images. Examples of such overlays are described with reference to FIGS. 11A to 13.

In certain embodiments, computer 30 determines a distance between eye 22 and patient interface 20 from the size of the outline of the liquid. After determining the distance, computer 30 may perform any suitable operation. For example, computer 30 may instruct display 36 to display the distance. As another example, computer 30 may instruct laser device 15 to adjust the actual distance in response to the determined distance. For example, computer 30 may determine that patient interface 20 is too close to eye 22, and may instruct laser device 15 to move interface away from eye 22. As another example, computer 30 may place an alignment overlay corresponding to the determined distance onto the images.

In certain embodiments, computer 30 performs a liquid distribution procedure to redistribute the liquid. Computer 30 may perform the procedure in any suitable manner. For example, computer 30 may instruct user and/or laser device 15 to move the patient interface closer to and/or farther away from eye 22. As another example, computer 30 may instruct liquid dispenser/vacuum 40 to dispense the additional liquid onto the outer surface of eye 22. As another example, computer 30 may instruct the vacuum device of liquid dispenser/vacuum 40 to remove a portion of the liquid from the outer surface of eye 22.

Figure 2A:
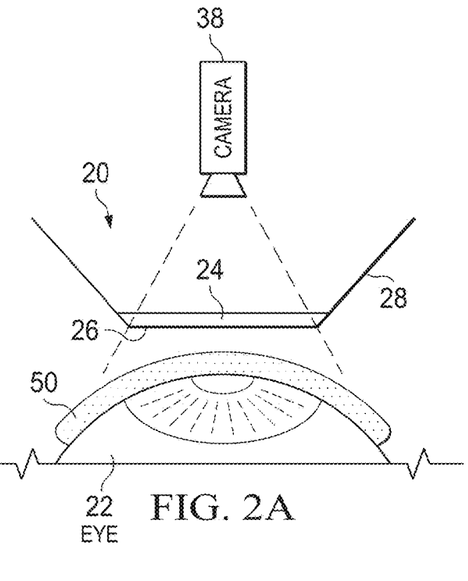
FIGS. 2A and 2B illustrate an example of a liquid disposed between an eye and a patient interface.

FIGS. 2A and 2B illustrate an example of a liquid 50 disposed between eye 22 and patient interface 20. FIG. 2A shows liquid 50 disposed between eye 22 and patient interface 20. Liquid 50 is not in contact with abutment face 26 of patient interface 20. Camera 38 records images of eye 22 through contact portion 24 of patient interface 20.

Figure 2B:
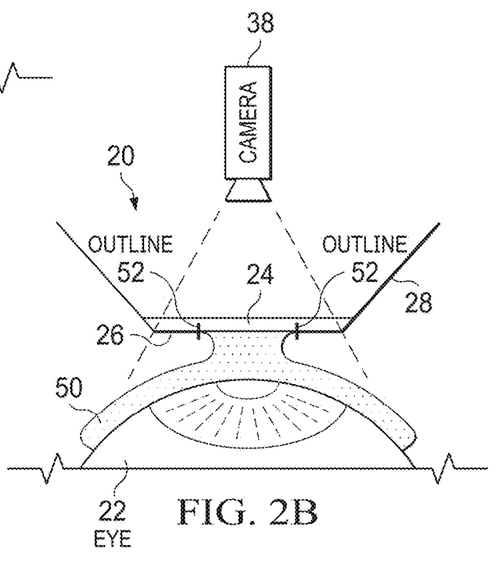

FIG. 2B shows liquid 50 in contact with abutment face 26. The adhesion of liquid 50 to abutment face 26 is stronger than the cohesive forces between the water molecules (also known as "capillary action") such that liquid 50 adheres to abutment face 26 and forms an outline 52 that can be imaged by camera 38. The shape of outline 52 is affected by the alignment of eye 22 with patient interface 20, and thus the shape can indicate the alignment of eye 22 with patient interface 20. Outline 52 can be formed on abutment face 26 prior to contact between the eye 22 itself and abutment face, so alignment of eye 22 with patient interface can start prior to contact. Examples of shapes of outline 52 are described with reference to FIG. 3.

Figure 3:
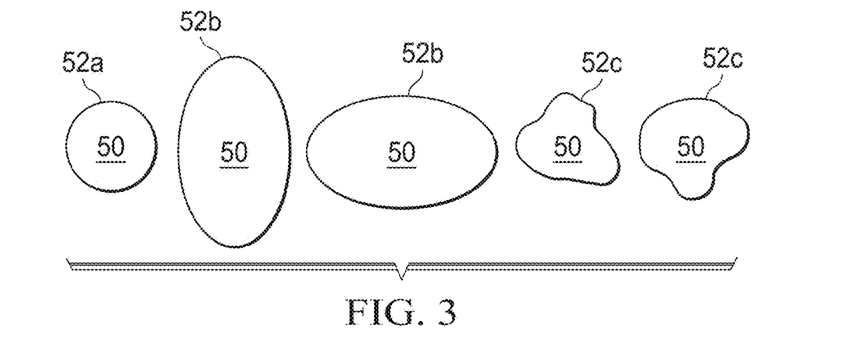
FIG. 3 illustrates examples of shapes of outlines of liquid.

FIG. 3 illustrates examples of shapes of outlines 52 (52*a*, 52*b*, 52*c*). Outline 52*a* has a round shape, which may indicate that eye 22 is aligned with patient interface 20. Outlines 52*b* have oval shapes, which may indicate that eye axis 27 is tilted relative to interface axis 25. Outlines 52*c* have shapes that are neither round nor oval, i.e., they are misshapen shapes, which may indicate that the cornea of eye 22 does not have a normal spherical shape, i.e., the shape is irregular. The relationships between the shapes of outline 52 and the alignment of eye 22 with patient interface 20 are described in more detail with reference to FIGS. 4A to 5B.

Figure 4A:
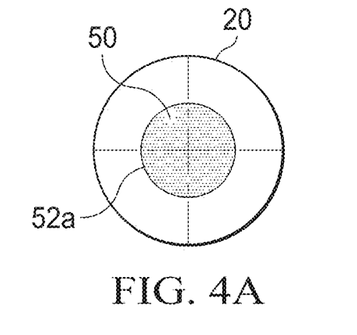
FIGS. 4A and 4B illustrate an example of how a round outline may indicate that an eye is aligned with a patient interface.
Figure 4B:
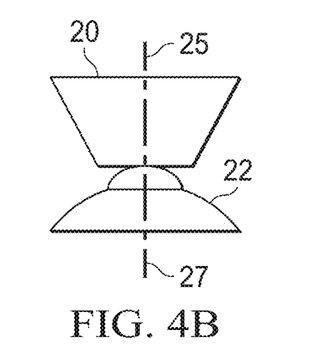

FIGS. 4A and 4B illustrate an example of how a round outline 52*a* may indicate that eye 22 is aligned with patient interface 20. Round outline 52*a* indicates that the distance between patient interface 20 and eye 22 is approximately the same at most (if not all) of the points of outline 52*a*, i.e., patient interface 20 is aligned symmetrically about the center (e.g., apex) of the cornea such that axis 27 of eye 22 is aligned with axis 25 of patient interface 20.

Figure 5A:
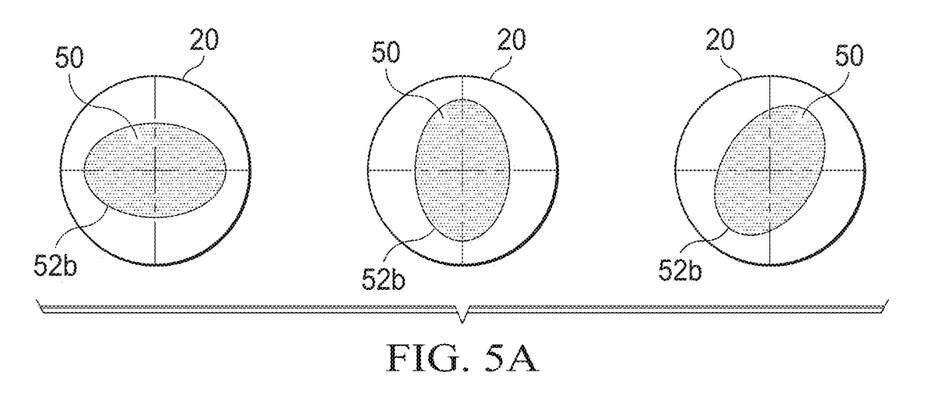
FIGS. 5A and 5B illustrate an example of how an oval outline may indicate that an eye axis is tilted relative to an interface axis.
Figure 5B:
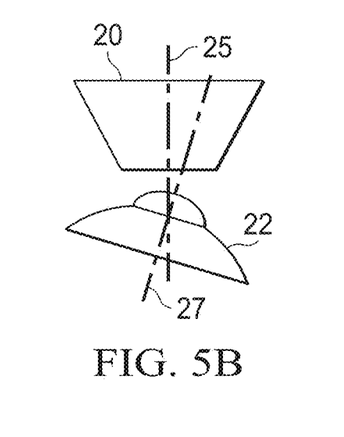

FIGS. 5A and 5B illustrate an example of how an oval outline 52*b* may indicate that eye axis 27 is tilted relative to interface axis 25 by an angle greater than zero degrees (e.g., greater than three degrees). The cornea is shaped such that oval outline 52*b* indicates that patient interface 20 is not aligned symmetrically about the apex of the cornea such that eye axis 27 is not aligned with interface axis 25, i.e., eye 22 may have a rolling misalignment. Note that the shape of eye 22 (e.g., prolate or oblate) also affects the shape of the oval. Rotating eye 22 relative to patient interface 20 (or patient interface 20 relative to eye 22) until outline 52 has a circular shape may compensate for the rolling misalignment.

Figure 6A:
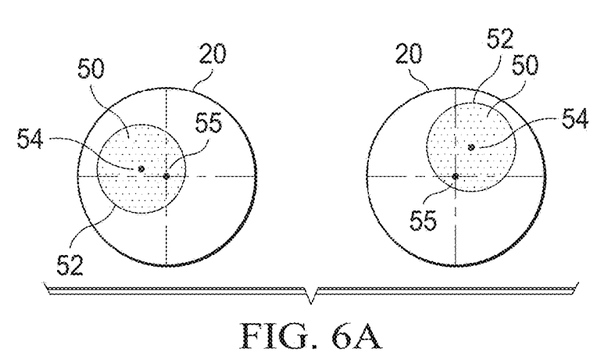
FIGS. 6A and 6B illustrate an example of how an outline may be used to correct lateral misalignment.
Figure 6B:
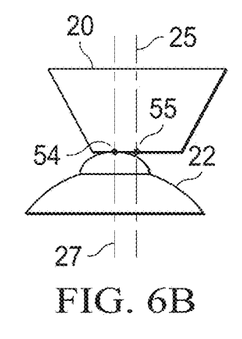

FIGS. 6A and 6B illustrate an example of how an outline 52 may be used to correct lateral misalignment. In certain embodiments, outline 52 has a center point 54 that should align with (x, y)=(0, 0) of the xyz-coordinate system of laser device 15, where the center 55 of abutment face 26 is (x, y)=(0, 0). In some cases, center point 54 may be the centroid of outline 52, which is the arithmetic mean position of all the points of the shape of outline 52. In the illustrated example, outline 52 is a round outline 52a, so center point 54 is the centroid, or the center, of the circle of outline 52a.

In the illustrated example, center point 54 is not located at abutment face center 55, so patient interface 20 is laterally misaligned with eye 22. Eye 22 may be laterally moved relative to patient interface 20 (or patient interface 20 may be laterally moved relative to eye 22) to correct the lateral misalignment.

Figure 7A:
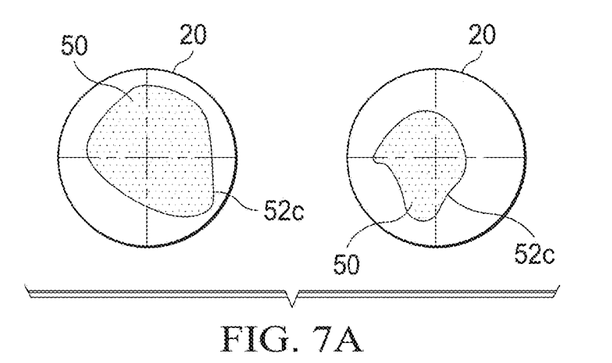
FIGS. 7A and 7B illustrate an example of a misshapen outline.
Figure 7B:
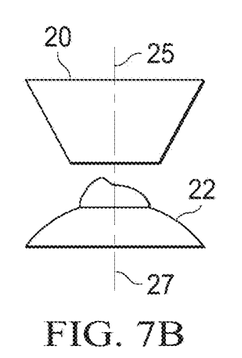

FIGS. 7A and 7B illustrate an example of a misshapen outline 52c.

Misshapen outline 52c indicates that the cornea of eye 22 has an irregular shape. In certain embodiments, computer 30 determines, from the corneal topography of eye 22, the desired outline 52 that indicates when patient interface 20 is aligned with eye 22. For example, computer 30 may calculate the distances between points of patient interface 20 and points of the cornea according to the corneal topography when patient interface 20 and eye 22 are aligned, and then determine the desired outline 52 of fluid 50 according to the distances. In certain embodiments, computer 30 may determine different desired outlines 52 for different stages of docking, e.g., when docking starts and eye 22 is farther away from patient interface 20, as docking proceeds and eye 22 is closer to patient interface 20, and when docking ends as patient interface 20 is affixed to eye 22. This is described in more detailed with reference to FIG. 13.

Figure 8:
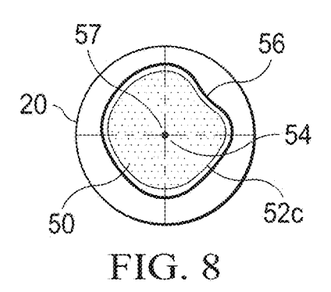
FIG. 8 illustrates an example of how an alignment overlay of an outline may be used to correct rolling, lateral, and/or torsional misalignment.

FIG. 8 illustrates an example of how an alignment overlay 56 of an outline 52c may be used to correct rolling, lateral, and/or torsional misalignment. In certain embodiments, computer 30 may generate an alignment overlay 56 that corresponds to the desired outline 50. Alignment overlay 56 may be displayed as an overlay on the recorded images, which may allow camera 38 and/or a user to detect and/or correct misalignment. In some cases, computer 30 adds a centering point 57 to alignment overlay 56. Centering point 57 may be located at abutment face center 55 and may allow camera 38 and/or a user to detect and/or correct lateral misalignment. In some cases, alignment overlay 56 may have a shape that allows camera 38 and/or a user to identify and/or correct torsional misalignment. If not, computer 30 may add one or more markers to alignment overlay 56 that allow camera 38 and/or a user to detect and/or correct torsional misalignment.

FIGS. 9A to 10B illustrate examples of graphical elements 58, 59, 60 that describe misalignments and adjustments for correcting the misalignments. In certain embodiments, computer 30 displays graphical elements 58 (58a to 58c), 59 (59a to 59c) that describe alignment or misalignment of eye 22 with patient interface 20. A graphical element 58, 59 may have any suitable size or shape that can indicate to the user alignment or misalignment of eye 22 with patient interface 20. In the illustrated example, graphical elements 58 (58a to 58c) show a side view of eye 22 relative to interface 20, and graphical elements 59 (59a to 59c) show a top view of outline 52 of liquid 50 relative to interface 20.

In certain embodiments, computer 30 displays graphical elements 60 (60a to 60e) that describe adjustments for correcting the misalignments or for continuing the docking process. Graphical elements 60 (60a to 60e) may assist a user in aligning eye 22 with patient interface 20. A graphical element 60 may have any suitable size or shape that can indicate to the user movement of patient interface 20 and/or eye 22. Examples of graphical elements 60 include: pointers (e.g., an arrows, line, or triangle or other polygon) that point towards a direction of movement; curved pointers that indicate a direction of rotation; and/or text that describes a direction of movement and/or rotation.

Figure 9A:
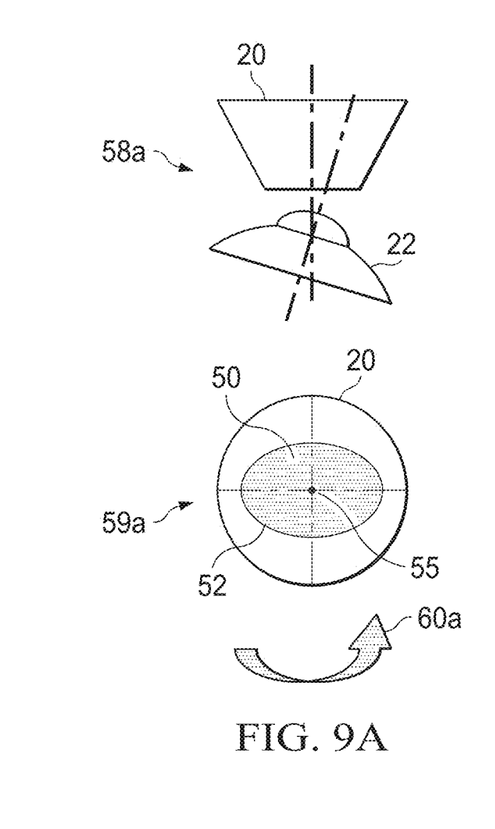
FIGS. 9A, 9B and 9C illustrate examples of graphical elements that describe misalignments and adjustments for correcting the misalignments.
Figure 9B:
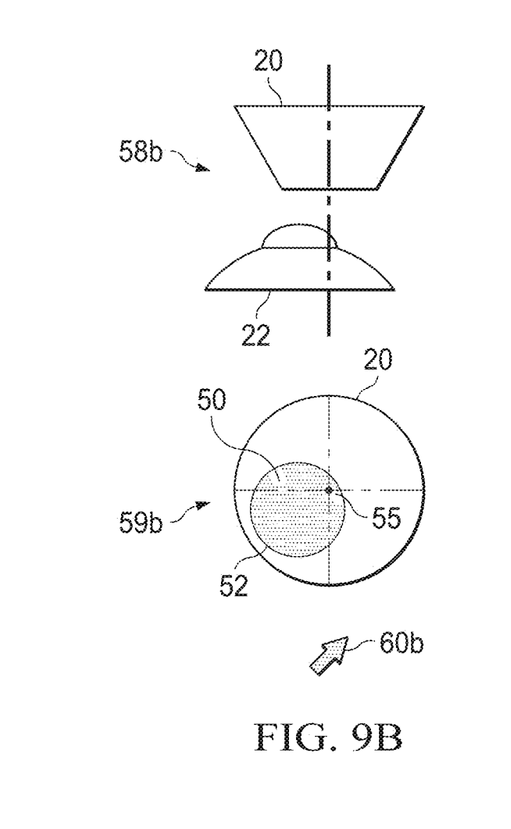
Figure 9C:
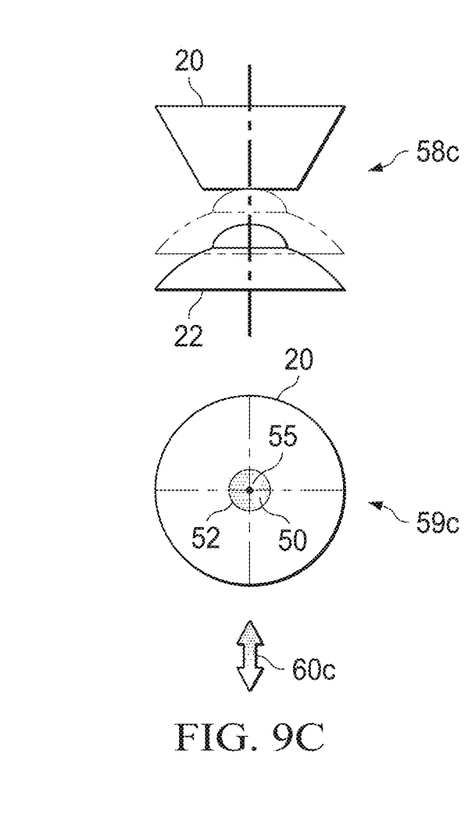

FIG. 9A shows a graphical element 60a that is a curved arrow representing a turning movement to turn eye 22 to align eye axis 27 with interface axis 25 to correct a rolling misalignment. FIG. 9B shows a graphical element 60b that is an arrow representing a translational movement to move the center point of outline 52 towards abutment face center 55. FIG. 9C shows a graphical element 60c that is an arrow representing a longitudinal movement to move eye 22 closer to patient interface 20.

Figure 10A:
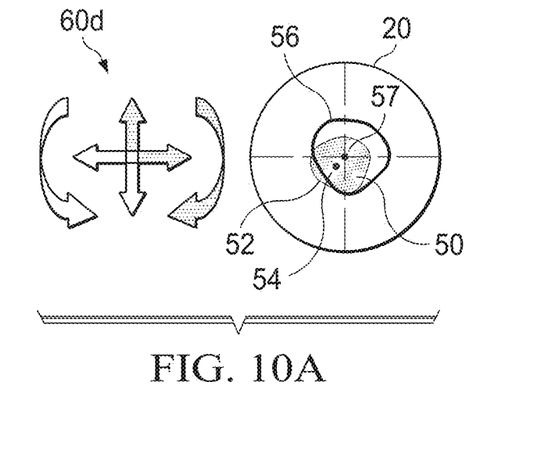
FIGS. 10A to 10B illustrate more examples of graphical elements that describe misalignments and adjustments for correcting the misalignments.
Figure 10B:
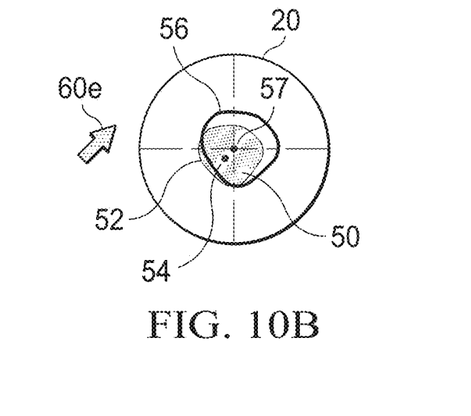

FIG. 10A shows a graphical element 60d that indicates two types of movement. The straight arrows represent a translational movement to move center point 54 of outline 52 towards centering point 57 of alignment overlay 56, and the curved arrows represent a rotational movement in the xy-plane to correct torsional misalignment. FIG. 10B shows a graphical element 60e that is an arrow representing a translational movement to move center point 54 of outline 52 towards centering point 57 of alignment overlay 56.

FIGS. 11A to 13 illustrate examples of the relationship between outline 52 of liquid 50 and the distance d between patient interface 20 and eye 22. In the examples, patient interface 20 has a planar abutment face. Patient interfaces 20 with a differently shaped abutment face may yield a differently shaped and/or sized outline 52.

Figure 11A:
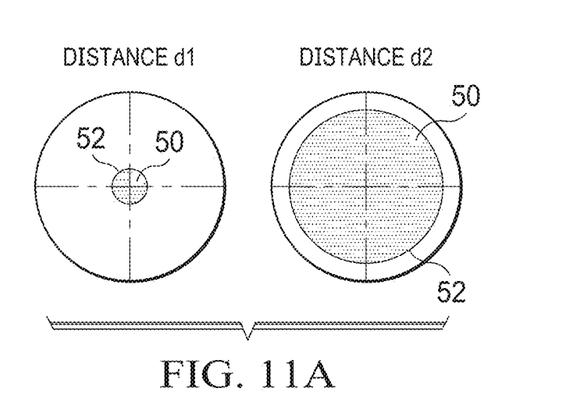
FIGS. 11A to 11B illustrate examples of the relationship between an outline and the distance between a patient interface and an eye.
Figure 11B:
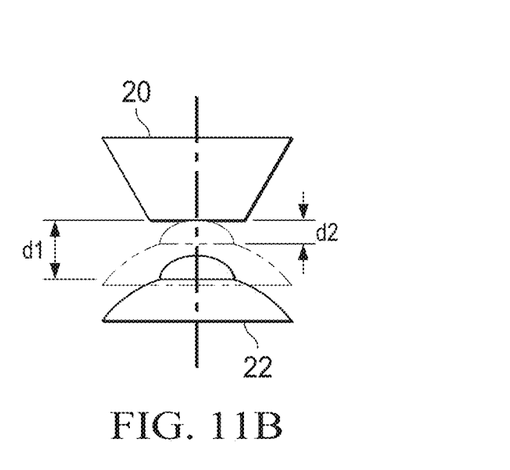

FIGS. 11A and 11B show outline 52 at distances d1 and d2, where d1>d2.

The distance d may be measured in any suitable manner. For example, the distance d may be measured as the distance between patient interface 20 (e.g., abutment face 16) and the base of the cornea (where the cornea meets the sclera) or other suitable part of the cornea. In general, outline 52 is smaller when distance d is larger, and becomes larger as distance d decreases, i.e., outline 52 becomes larger as eye 22 and interface 20 move closer relative to each other. In the example, outline 52 is smaller at distance d1 and larger at distance d2. The size of outline 52 may be measured in any suitable manner. For example, the size of outline 52 may be calculated from, e.g., the area bordered by outline 52 or a diameter of outline 52.

Figure 12A:
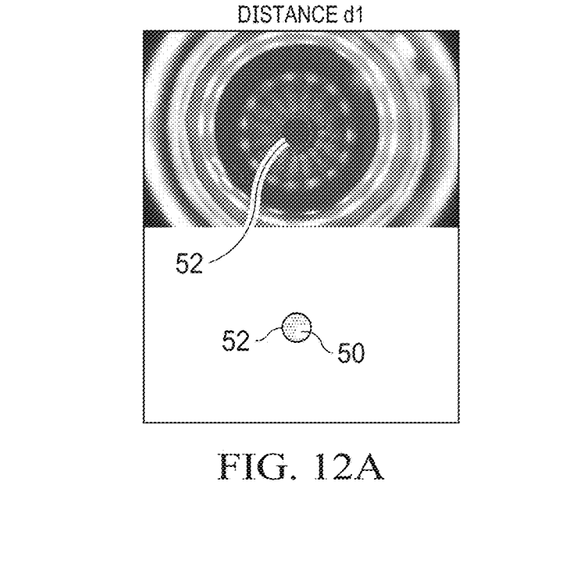
FIGS. 12A, 12B, and 12C illustrate more examples of the relationship between an outline and the distance between a patient interface and an eye.
Figure 12B:
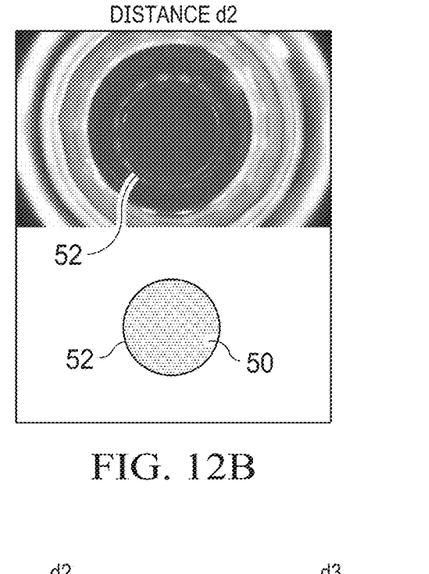
Figure 12C:
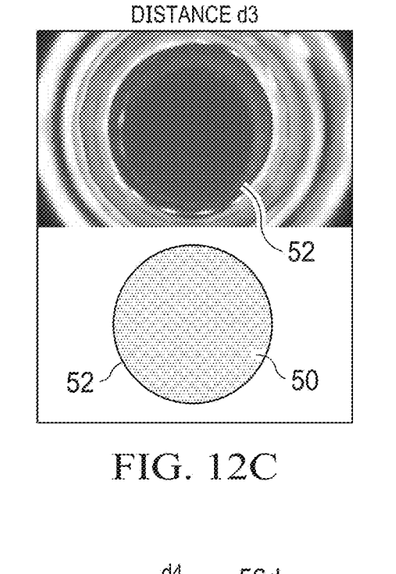

FIGS. 12A to 12C show outline 52 at distances d1, d2, and d3, where d1>d2>d3. In the example, outline 52 is smaller at distance d1, larger at distance d2, and even larger at distance d3. In the example, distance d1 may be a distance prior to contact between eye 22 and interface 20.

In certain embodiments, computer 30 calculates distance d from the size of outline 52. For example, computer 30 determines the relationship between the size of outline 52 and distance d. The relationship may be determined from, e.g., an average of previous measurements of size and distance or from the corneal topography of eye 22. Then, computer 30 measures the size of outline, and determines the distance from the size and relationship.

Figure 13:
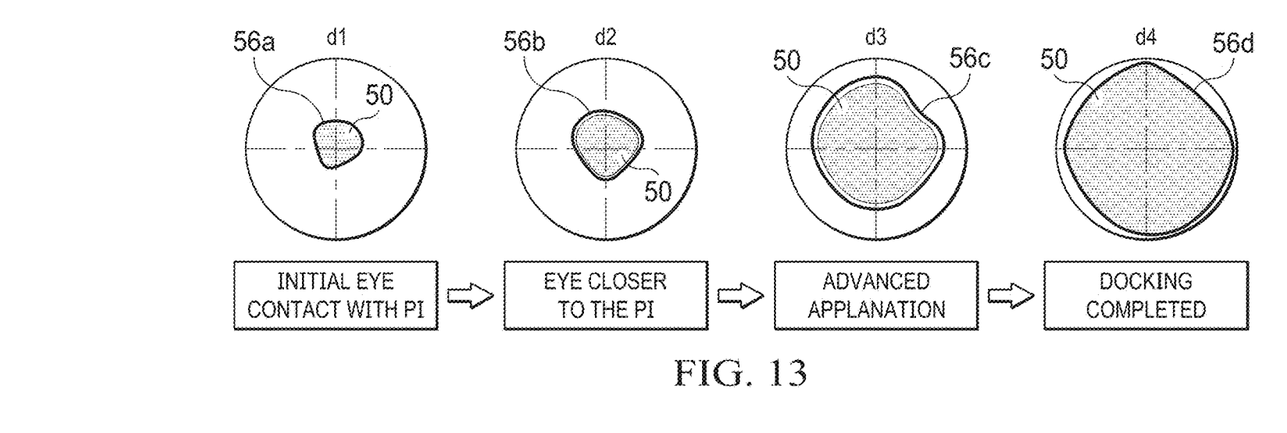
FIG. 13 illustrates different alignment overlays for different distances between a patient interface and an eye.

FIG. 13 illustrates different alignment overlays 56 for different distances d between patient interface 20 and eye 22. In certain embodiments, computer 30 determines the desired outline 52 (which indicates when patient interface 20 is aligned with eye 22) from the corneal topography of eye 22. The corneal topography of eye 22 generally describes the anterior shape of cornea. This shape can be translated into the xyz-coordinate system of laser device 15 such that the xy-coordinates of the surface of cornea can be determined for different z-values. Using this information, computer 30 predicts where the surface of the cornea touches abutment plate 26, as abutment plate 26 applies pressure to the cornea during docking. A predicted outline 52 borders where the surface of the cornea touches abutment plate 26. The predicted outline may serve as the desired outline 52.

In certain embodiments, computer 30 may determine different desired outlines 52 for different stages of docking, e.g., when docking starts and patient interface 20 is farther away from eye 22, as docking proceeds and patient interface 20 moves closer to eye 22, and when docking ends as patient interface 20 is affixed to eye 22. For example, computer 30 may predict, for each distance d between patient interface 20 and eye 22, an outline 52 that borders where the surface of the cornea touches abutment plate 26 according to the corneal topography of eye 22.

Computer 30 may also display an alignment overlay 56 (56a to 56d) corresponding to the desired outline 52 at each distance d during the different stages of docking. In the illustrated example, alignment overlay 56a represents the desired outline 52 at distance d1, when eye initially contacts patient interface 20. Alignment overlay 56b represents the desired outline 52 at distance d2, when eye moves closer patient interface 20. Alignment overlay 56c represents the desired outline 52 at distance d3, when eye is at advanced applanation with patient interface 20. Alignment overlay 56d represents the desired outline 52 at distance d4, when docking is completed.

In other examples, outline 52 can be formed on abutment face 26 prior to contact between the eye 22 itself and abutment face. In the examples, computer 30 determines an alignment overlay 56 corresponding to a desired outline 52 prior to contact, so alignment of eye 22 with patient interface 20 can start prior to contact.

Figure 14:
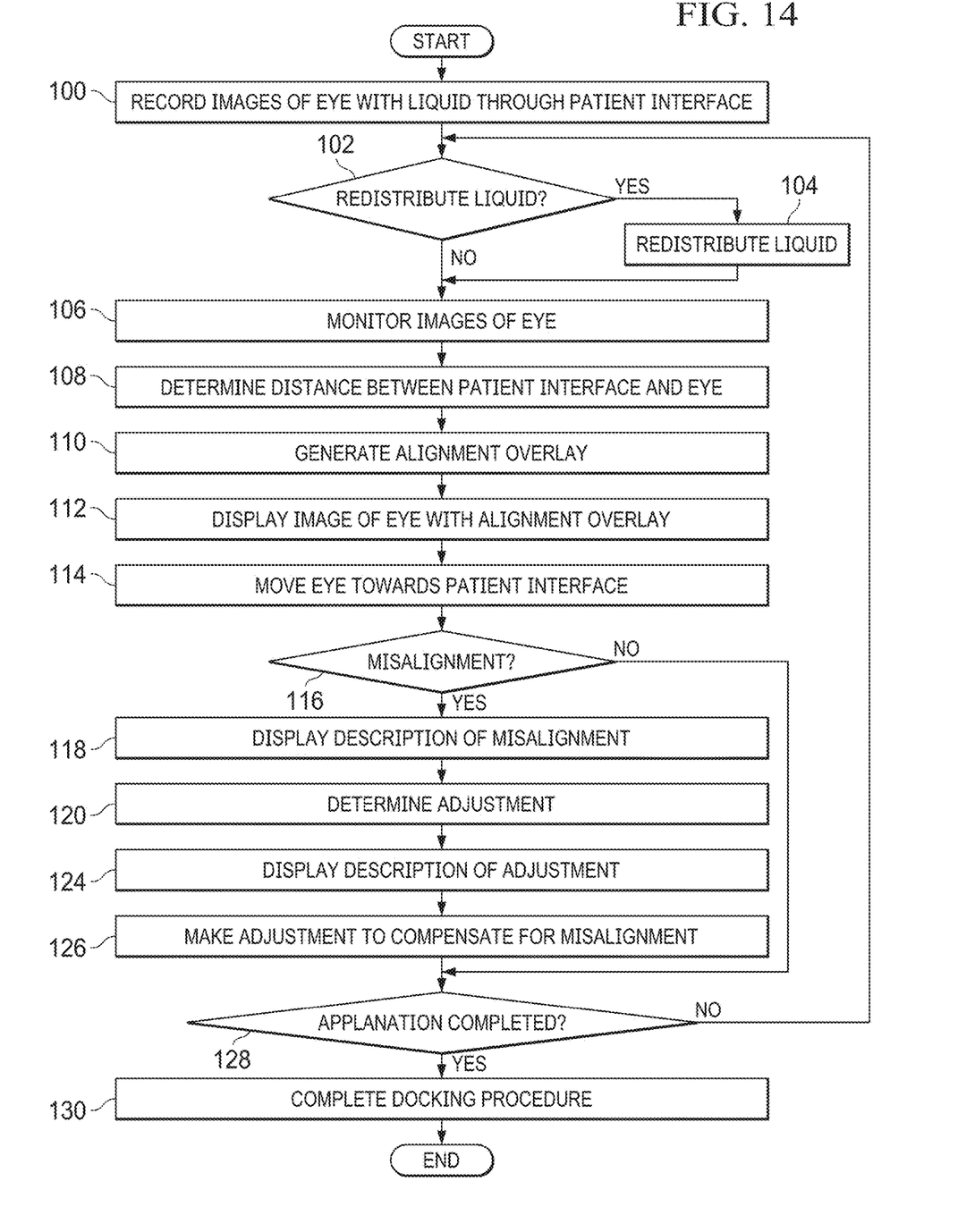
FIG. 14 illustrates an example of a method for aligning an eye with a patient interface that may be performed by the system of FIG. 1.

FIG. 14 illustrates an example of a method for aligning eye 22 with patient interface 20 that may be performed by system 10 of FIG. 1. The method starts at step 100, where camera 38 records images of eye 22 with liquid 50 through patient interface 20. Liquid (e.g., tear film) 50 is disposed between patient interface 20 and the outer surface of eye 22, and is in contact with patient interface 20 and the outer surface. The images include outline 52 of liquid 50.

Liquid 50 may be redistributed at step 102. For example, if outline 52 cannot be imaged by camera 38, liquid 50 may be redistributed. If liquid 50 is not to be redistributed, the method proceeds to step 106. If liquid 50 is to be redistributed, the method moves to step 104, where liquid 50 is redistributed. Computer 30 may perform a liquid distribution procedure in any suitable manner to redistribute liquid 50. For example, computer 30 may instruct the user and/or laser device 15 to move patient interface 20 closer to and/or farther away from eye 22, one or more times. As another example, computer 30 may instruct the user and/or the dispenser of liquid dispenser/vacuum 40 to dispense additional liquid onto the outer surface of eye 22. As another example, computer 30 may instruct the user and/or the vacuum device of liquid dispenser/vacuum 40 to remove a portion of the liquid from the outer surface of eye 22. After liquid 50 is redistributed, the method proceeds to step 106.

Computer 30 monitors the images of eye 22 at step 106, and determines distance d between patient interface 20 and eye 22 at step 108. In certain embodiments, computer 30 may determine distance d from the size of outline 52. In certain embodiments, computer 30 may instruct display screen 36 to display distance d. In certain embodiments, computer 30 may adjust distance d in response to the determined distance d.

Computer 30 generates alignment overlay 56 at step 110. In certain embodiments, computer 30 may generate an alignment overlay 56 that represents a desired outline 52 of liquid. In certain embodiments, computer 30 determines alignment overlay 56 from the corneal topography of eye 22. In certain embodiments, computer 30 determines a plurality of alignment overlays 56, where each alignment overlay 56 corresponds to a distance d between eye 22 and patient interface 20. When the docking process reaches a particular distance, the alignment overlay 56 corresponding to the distance is placed onto the images. Computer 30 instructs display 36 to display the image of eye 22 with alignment overlay 56 at step 112. Eye 22 is moved towards patient interface 20 or patient interface 20 is moved towards eye 22 at step 114. The relative movement may be made in any suitable manner. For example, the relative movement may be made in the xy-direction, torsionally, and/or z-direction in any suitable order.

There may be a misalignment at step 116. In certain embodiments, computer 30 identifies outline 52 in an image and determines misalignment of eye 22 from outline 52. For example, computer 30 may identify that outline 52 is an oval and determine that eye axis 27 is at an angle to interface axis 25. As another example, computer 30 may determine that the centroid of outline 52 not at a center point of laser device 15, and thus determine that eye 22 is laterally displaced with respect to the center point of laser device 15.

If there is no misalignment, the method proceeds to step 128, where the applanation may be completed. If there is a misalignment, computer 30 instructs display 36 to display a description of misalignment 58, 59 at step 118. Computer 30 determines an adjustment that compensates for the misalignment at step 120. In certain embodiments, computer 30 determines an adjustment that substantially compensates for the misalignment. For example, if the eye axis 27 is at an angle to interface axis 25, computer 30 may determine that rotating eye 22 substantially compensates for the misalignment. As another example, if eye 22 is laterally displaced a distance with respect to the center point of laser device 15, computer 30 may determine that one or more of the following substantially compensates for the misalignment: translating patient interface 20 the determined distance; translating eye 22 the determined distance towards the center point; and/or translating the treatment pattern the determined distance.

Computer 30 displays a description of the adjustment 60 at step 124. The adjustment may be made to compensate for the misalignment at step 126. For example, computer 30 may instruct laser device 15 to adjust patient interface 20 according to the adjustment to compensate for the misalignment. As another example, computer 30 may instruct an automated patient bed to change the position of the patient, such that eye 22 is moved according to the adjustment to compensate for the misalignment. As another example, computer 30 may adjust the treatment pattern according to the adjustment to compensate for the misalignment.

The applanation may be completed at step 128. If the applanation is not completed, the method returns to step 102, where liquid 50 may need to be distributed. If the applanation has been completed, the method proceeds to step 130, where the docking procedure is completed. The method then ends.

A component (e.g., computer 30) of the systems and apparatuses disclosed herein may include an interface, logic, and/or memory, any of which may include computer hardware and/or software. An interface (e.g., display 36) can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display screen, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A system for aligning an eye with a patient interface of a laser device, comprising:
    a camera configured to record a plurality of images of the eye through the patient interface of the laser device, a liquid disposed between the patient interface and an outer surface of the eye, the liquid in contact with the patient interface and with the outer surface of the eye, the images including an outline of the liquid;
    a display screen configured to display the images of the eye; and
    a computer configured to align the eye with the patient interface in order to align the eye with a laser beam of the laser device, the eye being aligned to perform a procedure on the eye according to a treatment pattern, the computer configured to align the eye with the patient interface by:
        identifying the outline of the liquid in an image received from the camera;
        determining a misalignment of the eye according to the outline; and
        instructing the display screen to display a description of the misalignment.

2. The system of claim 1, the computer configured to determine the misalignment of the eye according to the outline by:
    identifying that a shape of the outline is an oval; and
    determining that an axis of the eye is at an angle to a z-axis of the laser device.

3. The system of claim 1, the computer configured to determine the misalignment of the eye according to the outline by:
    determining that a centroid of a shape of the outline is not at a center point of the laser device
    determining that the eye is laterally displaced with respect to the center point of the laser device.

4. The system of claim 1, the computer configured to:
    determine an adjustment that substantially compensates for the misalignment.

5. The system of claim 4, the computer configured to determine the adjustment that substantially compensates for the misalignment by:
    identifying that a shape of the outline is an oval;
    determining that an axis of the eye is at an angle to a z-axis of the laser device in response to identifying the shape; and
    determine that rotating the eye substantially compensates for the misalignment.

6. The system of claim 4, the computer configured to determine the adjustment that substantially compensates for the misalignment by:
    determining that a centroid of a shape of the outline not at a center point of the laser device; and
    determining that the eye is laterally displaced a distance with respect to the center point of the laser device; and
    determining that translating the eye the determined distance towards the center point substantially compensates for the misalignment.

7. The system of claim 4, the computer configured to:
    instruct the display screen to display a description of the adjustment.

8. The system of claim 4, the computer configured to:
    adjust the patient interface or the eye according to the adjustment to compensate for the misalignment.

9. The system of claim 4, the computer configured to:
    adjust the treatment pattern according to the adjustment to compensate for the misalignment.

10. The system of claim 1, the computer configured to:
    generate an alignment overlay that indicates a desired position and a desired shape of the outline that aligns the eye with the patient interface;
    place the alignment overlay onto the images; and
    instruct the display screen to display the images with the alignment overlay.

11. The system of claim 10, the computer configured to:
    receive a description of a corneal topography of the eye; and
    determine the desired position and the desired shape of the outline that aligns the eye with the patient interface according to the corneal topography of the eye.

12. The system of claim 10, the computer configured to:
   determine a plurality of alignment overlays, each alignment overlay corresponding to a specific distance between the eye and the patient interface;
   determine the distance between the eye and the patient interface; and
   generate the alignment overlay corresponding to the determined distance.

13. The system of claim 1, the computer configured to:
   determine a distance between the eye and the patient interface according to a size of the outline.

14. The system of claim 13, the computer configured to instruct the display screen to display the distance between the eye and the patient interface.

15. The system of claim 13, the computer configured to adjust the distance of the eye from the patient interface in response to the determined distance between the eye and the patient interface.

16. The system of claim 1, the computer configured to perform a liquid distribution procedure to redistribute the liquid by:
   moving the patient interface farther away from the eye; and
   moving the patient interface closer to the eye.

17. The system of claim 1:
   further comprising a dispenser configured to dispense additional liquid onto the outer surface of the eye; and
   the computer configured to instruct the dispenser to dispense the additional liquid onto the outer surface of the eye.

18. The system of claim 17, the additional liquid comprising a substance that can change a surface tension of the liquid.

19. The system of claim 17, the additional liquid comprising a substance that enhances the visibility of the liquid.

20. The system of claim 1:
   further comprising a vacuum device configured to remove at least a portion of the liquid from the outer surface of the eye; and
   the computer configured to instruct the vacuum device to remove at least the portion of the liquid from the outer surface of the eye.

* * * * *